US007897168B2

(12) United States Patent
Chen et al.

(10) Patent No.: US 7,897,168 B2
(45) Date of Patent: Mar. 1, 2011

(54) DEGRADABLE POLYMERS INCORPORATING GAMMA-BUTYROLACTONE

(75) Inventors: Mingfei Chen, Santa Rosa, CA (US);
Peiwen Cheng, Santa Rosa, CA (US);
Ya Guo, Rohnert Park, CA (US);
Kishore Udipi, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 688 days.

(21) Appl. No.: 11/735,237

(22) Filed: Apr. 13, 2007

(65) Prior Publication Data
US 2008/0254085 A1    Oct. 16, 2008

(51) Int. Cl.
*A61F 2/00* (2006.01)
*A61F 2/82* (2006.01)
(52) U.S. Cl. .......................... 424/426; 424/422; 424/423
(58) Field of Classification Search .................. None
See application file for complete search history.

(56) References Cited

U.S. PATENT DOCUMENTS

| | | | | |
|---|---|---|---|---|
| 3,887,699 A | * | 6/1975 | Yolles | 424/477 |
| 5,747,390 A | * | 5/1998 | Cooper et al. | 442/59 |
| 5,854,383 A | | 12/1998 | Erneta et al. | |
| 6,015,815 A | | 1/2000 | Mollison | |
| 6,316,523 B1 | | 11/2001 | Hyon et al. | |
| 6,329,386 B1 | | 12/2001 | Mollison | |
| 7,166,570 B2 | * | 1/2007 | Hunter et al. | 514/2 |
| 7,713,272 B2 | * | 5/2010 | Roller et al. | 606/77 |

FOREIGN PATENT DOCUMENTS

| WO | WO 01/82970 | 11/2001 |
|---|---|---|
| WO | WO 2005/007195 | 1/2005 |

OTHER PUBLICATIONS

Moore et al., "Chemosynthesis of Bioresorbable Poly(Gamma-Butyrolactone) by Ring-Opening Polymerisation: a Review" Bio Materials, Elsevier Science Publishers Bv. Barking, GB, vol. 26, No. 18, Jun. 1, 2005, pp. 3771-3782.
Nakayama et al., "Synthesis and Biodegradability of Novel Copolyesters Containing Gamma-Butyrolactone Units" Polymer, Elsevier Science Publishers B.V., vol. 39, No. 5, Mar. 1, 1998 pp. 1213-1222.
Alt, Eckhard et al. "Inhibition of Neotima Formation After Experimental Coronary Artery Stenting" Circulation, 2000, pp. 1453-1458.

* cited by examiner

*Primary Examiner* — Robert A Wax
*Assistant Examiner* — Melissa S Mercier

(57) ABSTRACT

Disclosed herein are implantable medical devices having controlled release biodegradable polymer coatings thereon wherein the polymer is formed from ring opening of γ-butyrolactone and at least one additional monomer selected from the group consisting of trimethylene carbonate, lactide, polyethylene glycol, glycolide, the monomers formed from ring opening of ε-caprolactone, 4-tert-butyl caprolactone, and N-acetyl caprolactone, and combinations thereof, and at least one drug releasable from the biodegradable polymer. Also disclosed are implantable medical devices form of the biodegradable polymers and processes for forming the polymers.

6 Claims, 2 Drawing Sheets

DEGRADABLE POLYMERS INCORPORATING GAMMA-BUTYROLACTONE

FIELD OF THE INVENTION

The present invention relates to biodegradable copolymers formed from γ-butyrolactone for use in implantable medical devices and drug delivery systems.

BACKGROUND OF THE INVENTION

The role of polymers in the medical industry is rapidly growing. Polymers have seen use in surgical adhesives, sutures, tissue scaffolds, heart valves, vascular grafts and other medical and surgical products. One area that has seen noteworthy growth is implantable medical devices. Biocompatible polymers are particularly useful for manufacturing and coating implantable medical devices. Biodegradable biocompatible polymers suitable for coating and constructing medical devices generally include polyesters such as polylactide, polyglycolide, polycaprolactone, their copolymers or cellulose derivatives, collagen derivatives.

Properties advantageous for polymers used for medical devices include biocompatibility and, in some applications, biodegradability. The merits of biocompatible polymers include decreased inflammatory response, decreased immunological response and decreased post-surgical healing times. Biodegradability is advantageous for implanted medical devices since, in certain circumstances, the medical device would otherwise require a second surgery to remove the device after a period of time. Polymers can be rendered biodegradable biocompatible by modifying the monomer composition. In one example, an adhesive composition for surgical use was made biodegradable by copolymerizing caprolactone, ethylene glycol and DL lactic acid (see, for example, U.S. Pat. No. 6,316,523).

Additionally, polymers are used to deliver drugs from an implantable medical device made of another material wherein the polymer is coated on at least one surface of the medical device, thereby allowing for controlled drug release directly to the implantation site. Hydrophobic polymers including polylactic acid, polyglycolic acid and polycaprolactone are generally compatible with hydrophobic drugs. Hydrophilic polymers conversely are more compatible with hydrophilic drugs.

Implanted medical devices that are coated with biodegradable biocompatible polymers offer substantial benefits to the patient. Reduced inflammation and immunological responses promote faster post-implantation healing times in contrast to uncoated medical devices. Polymer-coated vascular stents, for example, may encourage endothelial cell proliferation and therefore integration of the stent into the vessel wall. Loading the coating polymers with appropriate drugs is also advantageous in preventing undesired biological responses. For example, an implanted polylactic acid polymer loaded with hirudin and prostacyclin does not generate thrombosis, a major cause of post-surgical complications (Eckhard et al., *Circulation*, 2000, pp 1453-1458).

There is therefore a need for improved polymeric materials suitable for drug delivery from implantable medical devices.

SUMMARY OF THE INVENTION

The present invention relates to biodegradable 4-hydroxybutyric acid ester—containing polymers suitable for use in implantable medical devices and drug delivery systems and able to control in situ drug release. The polymers of the present invention have polyester, polycarbonate and polyether backbones and are formed from γ-butyrolactone and at least one additional hydrophilic or hydrophobic monomer including, but not limited to, polyethylene glycol (PEG), trimethylene carbonate, lactide, p-dioxanone and ε-caprolactone.

The properties of biodegradable polymers are a result of the monomers used and the reaction conditions employed in their synthesis including, but not limited to, temperature, pressure, solvent choice, reaction time and catalyst choice.

In one embodiment of the present invention, an implantable medical device is provided having a controlled release biodegradable polymer coating thereon wherein the polymer is formed from ring opening of γ-butyrolactone and at least one additional monomer selected from the group consisting of trimethylene carbonate, lactide, polyethylene glycol, glycolide, ε-caprolactone, p-dioxanone, 4-tert-butyl caprolactone, and N-acetyl caprolactone, and at least one drug releasable from said biodegradable polymer.

In another embodiment of the present invention, an implantable medical device is provided comprising a controlled release biodegradable polymer wherein said polymer is formed from ring opening of γ-butyrolactone and at least one additional monomer selected from the group consisting of trimethylene carbonate, lactide, polyethylene glycol, glycolide, ε-caprolactone, p-dioxanone, 4-tert-butyl caprolactone, and N-acetyl caprolactone, and at least one drug releasable from said biodegradable polymer.

In another embodiment, the polymer comprises the general structure of Formula 6:

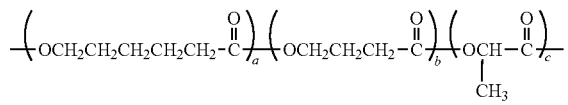

Formula 6 and wherein a is an integer from 1 to about 20,000; b is an integer from about 1 to about 20,000 and c is an integer from about 1 to about 20,000 and the sum of a, b and c is at least 3.

In another embodiment, the polymer comprises the general structure of Formula 7:

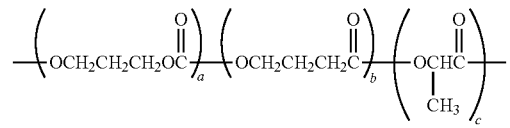

Formula 7 and wherein a is an integer from 1 to about 20,000; b is an integer from about 1 to about 20,000 and c is an integer from about 1 to about 20,000 and the sum of a, b and c is at least 3.

In another embodiment, the polymer comprises the general structure of Formula 8:

Formula 8 and wherein a is an integer from 1 to about 20,000; b is an integer from about 2 to about 20,000, and c is an integer from about 1 to about 20,000 and the sum of a, b and c is at least 3.

In another embodiment, the polymer comprises the general structure of Formula 9:

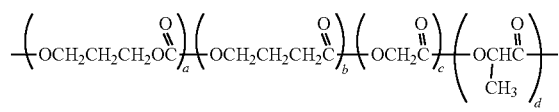

Formula 9 and wherein a is an integer from 1 to about 20,000; b is an integer from about 2 to about 20,000, and c is an integer from about 1 to about 20,000; d is an integer from about 1 to 20,000 and the sum of a, b and c is at least 4.

In yet another embodiment, the polymer comprises the general structure of Formula 10:

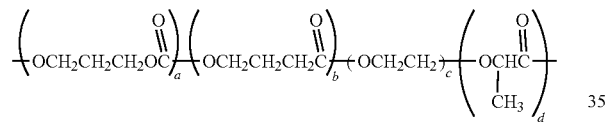

Formula 10 and wherein a is an integer from 1 to about 20,000; b is an integer from about 2 to about 20,000, and c is an integer from about 1 to about 20,000; d is an integer from about 1 to 20,000 and the sum of a, b and c is at least 4.

In another embodiment of the present invention, at least one drug is selected from the group consisting of FKBP-12 binding agents, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids. In yet another embodiment, the drug comprises at least one compound selected from the group consisting of sirolimus (rapamycin), tacrolimus (FK506), everolimus (certican), temsirolimus (CCI-779) and zotarolimus (ABT-578). In another embodiment the drug comprises zotarolimus.

In another embodiment, the implantable medical device is selected from the group consisting of vascular stents, stent grafts, urethral stents, bile duct stents, catheters, guide wires, pacemaker leads, bone screws, sutures and prosthetic heart valves. In another embodiment, the implantable medical device is a vascular stent.

In yet another embodiment of the present invention, the implantable medical device further comprises a cap coat.

In one embodiment of the present invention, a process is provided for the preparation of a biodegradable polymer comprising the step of performing a ring-opening polymerization reaction of γ-butyrolactone and at least one monomer selected from the group consisting of trimethylene carbonate, lactide, polyethylene glycol, glycolide, ε-caprolactone, p-dioxanone, 4-tert-butyl caprolactone, and N-acetyl caprolactone, in the presence of a catalyst selected from the group consisting of aluminum triisopropoxide (Al(iPrO)$_3$), tin (II) octoate, tetraphenyl tin, titanium (IV) isopropoxide and zirconium (IV) isopropoxide.

DEFINITION OF TERMS

Figure 1:
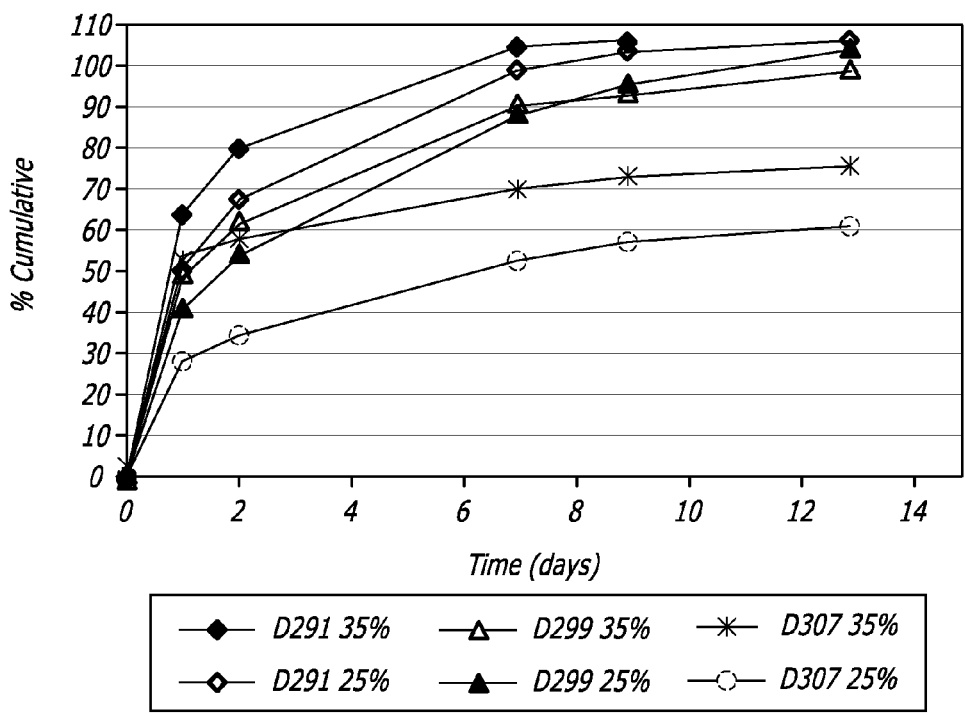
FIG. 1 depicts the release of ABT-578 from biodegradable polymer-coated stents according to the teachings of the present invention.

Prior to setting forth the invention, it may be helpful to an understanding thereof to set forth definitions of certain terms that will be used hereinafter:

γ-butyrolactone: As used herein γ-butyrolactone (gamma-butyrolactone) refers to a molecule having the general structure of Formula 1.

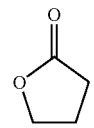

Formula 1

Lactide: As used herein, lactide refers to 3,6-dimethyl-1,4-dioxane-2,5-dione. More commonly lactide is also referred to herein as the heterodimer of R and S forms of lactic acid, the homo-dimer of the S form of lactic acid and the homodimer of the R form of lactic acid. Lactide is also depicted below in Formula 2. Lactic acid and lactide are used interchangeably herein.

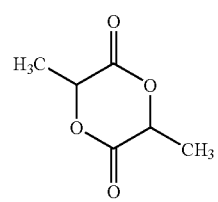

Formula 2

Glycolide: As used herein, glycolide refers to a molecule having the general structure of Formula 3.

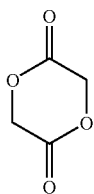

Formula 3

4-tert-butyl caprolactone: As used herein 4-tert-butyl caprolactone refers to a molecule having the general structure of Formula 4.

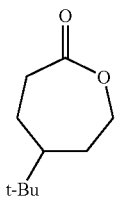

Formula 4

N-acetyl caprolactone: As used herein N-acetyl caprolactone refers to a molecule having the general structure of Formula 5.

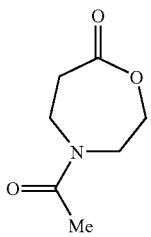

Formula 5

Backbone: As used here in "backbone" refers to the main chain of a polymer or copolymer of the present invention. A "polyester backbone" as used herein refers to the main chain of a biodegradable polymer comprising ester linkages. A "polyether backbone" as used herein refers to the main chain of a biodegradable polymer comprising ether linkages. An exemplary polyether is polyethylene glycol (PEG).

Biocompatible: As used herein "biocompatible" shall mean any material that does not cause injury or death to the animal or induce an adverse reaction in an animal when placed in intimate contact with the animal's tissues. Adverse reactions include inflammation, infection, fibrotic tissue formation, cell death, or thrombosis.

Biodegradable: As used herein "biodegradable" refers to a polymeric composition that is biocompatible and subject to being broken down in vivo through the action of normal biochemical pathways. From time-to-time bioresorbable and biodegradable may be used interchangeably, however they are not coextensive. Biodegradable polymers may or may not be reabsorbed into surrounding tissues, however all bioresorbable polymers are considered biodegradable. The biodegradable polymers of the present invention are capable of being cleaved into biocompatible byproducts through chemical- or enzyme-catalyzed hydrolysis.

Copolymer: As used here in a "copolymer" will be defined as a macromolecule produced by the simultaneous or stepwise polymerization of two or more dissimilar units such as monomers. Copolymer shall include bipolymers (two dissimilar units), terpolymers (three dissimilar units), etc.

Controlled release: As used herein "controlled release" refers to the release of a bioactive compound from a medical device surface at a predetermined rate. Controlled release implies that the bioactive compound does not come off the medical device surface sporadically in an unpredictable fashion and does not "burst" off of the device upon contact with a biological environment (also referred to herein a first order kinetics) unless specifically intended to do so. However, the term "controlled release" as used herein does not preclude a "burst phenomenon" associated with deployment. In some embodiments of the present invention an initial burst of drug may be desirable followed by a more gradual release thereafter. The release rate may be steady state (commonly referred to as "timed release" or zero order kinetics), that is the drug is released in even amounts over a predetermined time (with or without an initial burst phase) or may be a gradient release. A gradient release implies that the concentration of drug released from the device surface changes over time.

Drug(s): As used herein "drug" shall include any bioactive agent, pharmaceutical compound or molecule having a therapeutic effect in an animal. Exemplary, non-limiting examples include anti-proliferatives including, but not limited to, macrolide antibiotics including FKBP 12 binding compounds, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides, and transforming nucleic acids. Bioactive agents can also include cytostatic compounds, chemotherapeutic agents, analgesics, statins, nucleic acids, polypeptides, growth factors, and delivery vectors including, but not limited to, recombinant microorganisms, and liposomes.

Exemplary FKBP 12 binding compounds include sirolimus (rapamycin), tacrolimus (FK506), everolimus (certican or RAD-001), temsirolimus (CCI-779 or amorphous rapamycin 42-ester with 3-hydroxy-2-(hydroxymethyl)-2-methylpropionic acid) and zotarolimus (ABT-578). Additionally, and other rapamycin hydroxyesters may be used in combination with the polymers of the present invention.

Ductility: As used herein "ductility, or ductile" is a polymer attribute characterized by the polymer's resistance to fracture or cracking when folded, stressed or strained at operating temperatures. When used in reference to the polymer coating compostions of the present invention the normal operating temperature for the coating will be between room temperature and body temperature or approximately between 15° C. and 40° C. Polymer durability in a defined environment is often a function of its elasticity/ductility.

Glass Transition Temperature (Tg): As used herein glass transition temperature (Tg) refers to a temperature wherein a polymer structurally transitions from a elastic pliable state to a rigid and brittle state.

Hydrophilic: As used herein in reference to the bioactive agent, the term "hydrophilic" refers to a bioactive agent that has a solubility in water of more than 200 micrograms per milliliter.

Hydrophobic: As used herein in reference to the bioactive agent the term "hydrophobic" refers to a bioactive agent that has a solubility in water of no more than 200 micrograms per milliliter.

$M_n$: As used herein $M_n$ refers to number-average molecular weight. Mathematically it is represented by the following formula:

$M_n = \Sigma_i N_i M_i / \Sigma_i N_i$, wherein the $N_i$ is the number of moles whose weight is $M_i$.

$M_w$: As used herein $M_w$ refers to weight average molecular weight that is the average weight that a given polymer may have. Mathematically it is represented by the following formula:

$M_w = \Sigma_i N_i M_i^2 / \Sigma_i N_i M_i$, wherein $N_i$ is the number of molecules whose weight is $M_i$.

DETAILED DESCRIPTION OF THE INVENTION

Disclosed herein are biodegradable polymers suitable for use in forming and coating implantable medical devices and drug delivery systems that control in situ drug release. The polymers of the present invention have polyester, carbonate and polyether backbones and are comprised of monomer units formed from the ring opening of γ-butyrolactone and at least one additional hydrophilic or hydrophobic monomer including, but not limited to, ε-caprolactone, polyethylene glycol (PEG), trimethylene carbonate, lactide, glycolide, p-dioxanone and their derivatives.

Structural integrity and mechanical durability are provided through the incorporation of monomers such as, but not limited to, lactide. Elasticity and hydrophobicity is provided by monomers such as, but not limited to, caprolactone, γ-butyrolactone and trimethylene carbonate. Incorporation of PEG monomers provides a hydrophilic characteristic to the resulting polymer. The biodegradable 4-hydroxybutyric acid ester-containing polymers of the present invention are amphiphilic and provide both hydrophobic and hydrophilic drug loading capability.

During the synthesis of the biodegradable containing polymers of the present invention, the monomer ratios are varied to allow the ordinarily skilled practitioner to fine tune, or to modify, the properties of the polymer. The properties of biodegradable polymers arise from the monomers used and the reaction conditions employed in their synthesis including but not limited to, temperature, solvents, reaction time and catalyst choice. Catalysts are optional components of the synthesis reactions for forming the polymers and suitable catalysts include, but are not limited to aluminum triisopropoxide (Al (iPrO)$_3$), tin (II) octoate, tetraphenyl tin, titanium (IV) isopropoxide and zirconium (IV) isopropoxide.

The present invention also takes into account fine tuning, or modifying, the glass transition temperature (Tg) of the biodegradable polymers. Drug elution from polymers depends on many factors including, without limitation, density, the drug to be eluted, molecular composition of the polymer and Tg. Higher Tgs, for example temperatures above 40° C., result in more brittle polymers while lower Tgs, e.g lower than 40° C., result in more pliable and elastic polymers at higher temperatures. Drug elution is slow from polymers that have high Tgs while faster rates of drug elution are observed with polymers possessing low Tgs. In one embodiment of the present invention, the Tg of the polymer is selected to be lower than 37° C.

In one embodiment, the polymers of the present invention can be used to fabricate and coat medical devices. Coating polymers having relatively high Tgs can result in medical devices with unsuitable drug eluting properties as well as unwanted brittleness. In the cases of polymer-coated vascular stents, a relatively low Tg in the coating polymer effects the deployment of the vascular stent. For example, polymer coatings with low Tgs are "sticky" and adhere to the balloon used to expand the vascular stent during deployment, causing problems with the deployment of the stent. Low Tg polymers, however, have beneficial features in that polymers having low Tgs are more elastic at a given temperature than polymers having higher Tgs. Expanding and contracting a polymer-coated vascular stent mechanically stresses the coating. If the coating is too brittle, i.e. has a relatively high Tg, then fractures may result in the coating possibly rendering the coating inoperable. If the coating is elastic, i.e has a relatively low Tg, then the stresses experienced by the coating are less likely to mechanically alter the structural integrity of the coating. Therefore, the Tgs of the polymers of the present invention can be fine tuned for appropriate coating applications by a combination of monomer composition and synthesis conditions. The polymers of the present invention are engineered to have adjustable physical properties enabling the practitioner to choose the appropriate polymer for the appropriate medical function.

In order to tune, or modify, the polymers of the present invention, a variety of properties are considered including, but not limited to, Tg, molecular connectivity, molecular weight and thermal properties.

In the present invention, the balance between the hydrophobic and hydrophilic monomers in the biodegradable polymer is controlled. Drug-eluting properties of the biodegradable polymers can therefore be tailored to a wide range of drugs. For example, increasing the hydrophobic nature of the polymer increases the polymer's compatibility with hydrophobic drugs. Furthermore, when the polymer is to be used as a coating, they can be tailored to adhere to a particular surface. In one embodiment of the invention, polyethylene glycol (PEG) is used to impart a hydrophilic nature to the polymer. A wide range of PEGs are used within molecular weights ($M_n$) ranging from about 100 to about 4000.

The biodegradable polymers used to form the coatings and implantable medical devices of the present invention can generally be described as follows:

In one embodiment of the present invention, a polymer is prepared from the monomers ε-caprolactone, γ-butyrolactone and lactide. These monomers are polymerized in the presence of tin (II) octoate catalyst. An exemplary polymer produced with these monomers has the composition of Formula 6:

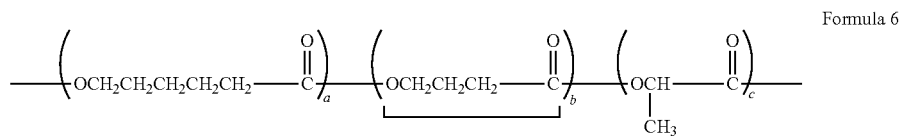

Formula 6

4-hydroxybutyric acid residual

In one embodiment of the polymer of Formula 6, a is an integer from 1 to about 20,000; b is an integer from about 1 to about 20,000; c is an integer from about 1 to about 20,000 and the sum of a, b and c is at least 3. In additional embodiments, a is an integer from 10 to about 19,000; from 100 to 18,000, from 200 to 17,000; from 300 to 16,000; from 400 to 15,000; from 500 to 14,000; from 600 to 13,000; from 700 to 12,000; from 800 to 11,000; from 900 to 10,000; from 1,000 to 9,000; from 1,100 to 8,000; from 1,200 to 7,000; from 1,300 to about 6,000; from 1,400 to 5,000; from 1,500 to 4,000; from 1,600 to 3,000; from 1,700 to 2,000; or from 1,800 to 1,900. In additional embodiments, b is an integer from 10 to about 19,000; from 100 to 18,000, from 200 to 17,000; from 300 to 16,000; from 400 to 15,000; from 500 to 14,000; from 600 to 13,000; from 700 to 12,000; from 800 to 11,000; from 900 to 10,000; from 1,000 to 9,000; from 1,100 to 8,000; from 1,200 to 7,000; from 1,300 to about 6,000; from 1,400 to 5,000; from 1,500 to 4,000; from 1,600 to 3,000; from 1,700 to 2,000; or from 1,800 to 1,900. In additional embodiments, c is an integer from 10 to about 19,000; from 100 to 18,000, from 200 to 17,000; from 300 to 16,000; from 400 to 15,000; from 500 to 14,000; from 600 to 13,000; from 700 to 12,000; from 800 to 11,000; from 900 to 10,000; from 1,000 to 9,000; from 1,100 to 8,000; from 1,200 to 7,000; from 1,300 to about 6,000; from 1,400 to 5,000; from 1,500 to 4,000; from 1,600 to 3,000; from 1,700 to 2,000; or from 1,800 to 1,900. With control over the variation in a, b and c, the practitioner is able to tune the physical properties of the biodegradable polymers.

In one embodiment of the present invention, a polymer is prepared from the monomers trimethylene carbonate, γ-butyrolactone and lactide. These monomers are polymerized in the presence of aluminum triisopropoxide catalyst. An exemplary polymer produced with these monomers has the composition of Formula 7:

Formula 7

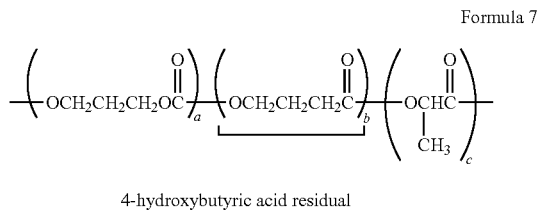

4-hydroxybutyric acid residual

In one embodiment of the polymer of Formula 7, a is an integer from 1 to about 20,000; b is an integer from about 1 to about 20,000; c is an integer from about 1 to about 20,000 and the sum of a, b and c is at least 3. In additional embodiments, a is an integer from 10 to about 19,000; from 100 to 18,000, from 200 to 17,000; from 300 to 16,000; from 400 to 15,000; from 500 to 14,000; from 600 to 13,000; from 700 to 12,000; from 800 to 11,000; from 900 to 10,000; from 1,000 to 9,000; from 1,100 to 8,000; from 1,200 to 7,000; from 1,300 to about 6,000; from 1,400 to 5,000; from 1,500 to 4,000; from 1,600 to 3,000; from 1,700 to 2,000; or from 1,800 to 1,900. In additional embodiments, b is an integer from 10 to about 19,000; from 100 to 18,000, from 200 to 17,000; from 300 to 16,000; from 400 to 15,000; from 500 to 14,000; from 600 to 13,000; from 700 to 12,000; from 800 to 11,000; from 900 to 10,000; from 1,000 to 9,000; from 1,100 to 8,000; from 1,200 to 7,000; from 1,300 to about 6,000; from 1,400 to 5,000; from 1,500 to 4,000; from 1,600 to 3,000; from 1,700 to 2,000; or from 1,800 to 1,900. In additional embodiments, c is an integer from 10 to about 19,000; from 100 to 18,000, from 200 to 17,000; from 300 to 16,000; from 400 to 15,000; from 500 to 14,000; from 600 to 13,000; from 700 to 12,000; from 800 to 11,000; from 900 to 10,000; from 1,000 to 9,000; from 1,100 to 8,000; from 1,200 to 7,000; from 1,300 to about 6,000; from 1,400 to 5,000; from 1,500 to 4,000; from 1,600 to 3,000; from 1,700 to 2,000; or from 1,800 to 1,900. With control over the variation in a, b and c, the practitioner is able to tune the physical properties of the biodegradable polymers.

In another embodiment of the present invention, a polymer is prepared from the monomers trimethylene carbonate, γ-butyrolactone, and glycolide. An exemplary polymer produced with these monomers has the composition of Formula 8:

Formula 8

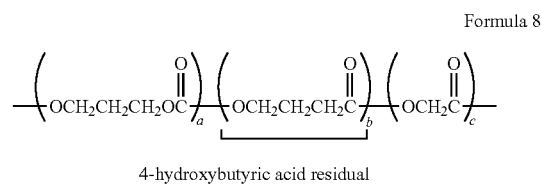

4-hydroxybutyric acid residual

In one embodiment of the polymer of Formula 8, a is an integer from 1 to about 20,000; b is an integer from about 1 to about 20,000; c is an integer from about 1 to about 20,000 and the sum of a, b and c is at least 3. In additional embodiments, a is an integer from 10 to about 19,000; from 100 to 18,000, from 200 to 17,000; from 300 to 16,000; from 400 to 15,000; from 500 to 14,000; from 600 to 13,000; from 700 to 12,000; from 800 to 11,000; from 900 to 10,000; from 1,000 to 9,000; from 1,100 to 8,000; from 1,200 to 7,000; from 1,300 to about 6,000; from 1,400 to 5,000; from 1,500 to 4,000; from 1,600 to 3,000; from 1,700 to 2,000; or from 1,800 to 1,900. In additional embodiments, b is an integer from 10 to about 19,000; from 100 to 18,000, from 200 to 17,000; from 300 to 16,000; from 400 to 15,000; from 500 to 14,000; from 600 to 13,000; from 700 to 12,000; from 800 to 11,000; from 900 to 10,000; from 1,000 to 9,000; from 1,100 to 8,000; from 1,200 to 7,000; from 1,300 to about 6,000; from 1,400 to 5,000; from 1,500 to 4,000; from 1,600 to 3,000; from 1,700 to 2,000; or from 1,800 to 1,900. In additional embodiments, c is an integer from 10 to about 19,000; from 100 to 18,000, from 200 to 17,000; from 300 to 16,000; from 400 to 15,000; from 500 to 14,000; from 600 to 13,000; from 700 to 12,000; from 800 to 11,000; from 900 to 10,000; from 1,000 to 9,000; from 1,100 to 8,000; from 1,200 to 7,000; from 1,300 to about 6,000; from 1,400 to 5,000; from 1,500 to 4,000; from 1,600 to 3,000; from 1,700 to 2,000; or from 1,800 to 1,900. With control over the variation in a, b and c, the practitioner is able to tune the physical properties of the biodegradable polymers.

In another embodiment of the present invention, a polymer is prepared from the monomers trimethylene carbonate, γ-butyrolactone, lactide, and glycolide. An exemplary polymer produced with these monomers has the composition of Formula 9:

Formula 9

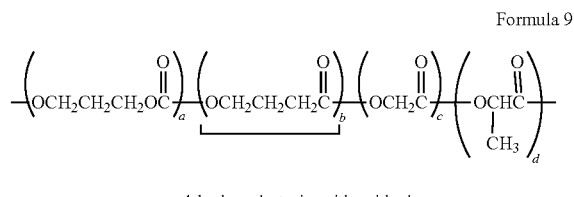

4-hydroxybutyric acid residual

In one embodiment of the polymer of Formula 9, a is an integer from 1 to about 20,000; b is an integer from about 1 to about 20,000; c is an integer from about 1 to about 20,000 and the sum of a, b and c is at least 4. In additional embodiments, a is an integer from 10 to about 19,000; from 100 to 18,000, from 200 to 17,000; from 300 to 16,000; from 400 to 15,000; from 500 to 14,000; from 600 to 13,000; from 700 to 12,000; from 800 to 11,000; from 900 to 10,000; from 1,000 to 9,000; from 1,100 to 8,000; from 1, to 7,000; from 1,300 to about 6,00; from 1,400 to 5,000; from 1,500 to 4,000; from 1,600 to 3,000; from 1,700 to 2,000; or from 1,800 to 1,900. In additional embodiments, b is an integer from 10 to about 19,000; from 100 to 18,000, from 200 to 17,000; from 300 to 16,000; from 400 to 15,000; from 500 to 14,000; from 600 to 13,000; from 700 to 12,000; from 800 to 11,000; from 900 to 10,000; from 1,000 to 9,000; from 1,100 to 8,000; from 1,200 to 7,000; from 1,300 to about 6,000; from 1,400 to 5,000; from 1, to 4,000; from 1,600 to 3,000; from 1,700 to 2,000; or from 1,800 to 1,900. In additional embodiments, c is an integer from 10 to about 19,000; from 100 to 18,000, from 200 to 17,000; from 300 to 16,000; from 400 to 15,000; from 500 to 14,000; from 600 to 13,000; from 700 to 12,000; from 800 to 11,000; from 900 to 10,000; from 1,000 to 9,000; from 1,100 to 8,000; from 1,200 to 7,000; from 1,300 to about 6,000; from 1,400 to 5,000; from 1,500 to 4,000; from 1,600 to 3,000; from 1,700 to 2,000; or from 1,800 to 1,900. With control over the variation in a, b and c, the practitioner is able to tune the physical properties of the biodegradable polymers.

In another embodiment of the present invention, a polymer is prepared from the monomers trimethylene carbonate, γ-butyrolactone, lactide, and PEG. An exemplary polymer produced with these monomers has the composition of Formula 10:

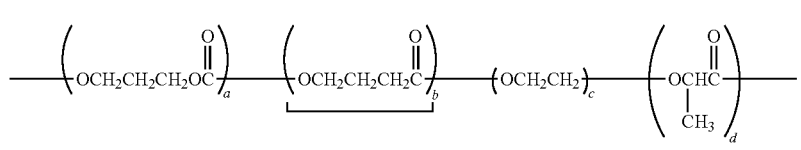

Formula 10

4-hydroxybutyric acid residual

In one embodiment of the polymer of Formula 10, a is an integer from 1 to about 20,000; b is an integer from about 1 to about 20,000; c is an integer from about 1 to about 20,000 and the sum of a, b and c is at least 4. In additional embodiments, a is an integer from 10 to about 19,000; from 100 to 18,000, from 200 to 17,000; from 300 to 16,000; from 400 to 15,000; from 500 to 14,000; from 600 to 13,000; from 700 to 12,000; from 800 to 11,000; from 900 to 10,000; from 1,000 to 9,000; from 1,100 to 8,000; from 1, to 7,000; from 1,300 to about 6,000; from 1,400 to 5,000; from 1,500 to 4,000; from 1,600 to 3,000; from 1,700 to 2,000; or from 1,800 to 1,900. In additional embodiments, b is an integer from 10 to about 19,000; from 100 to 18,000, from 200 to 17,000; from 300 to 16,000; from 400 to 15,000; from 500 to 14,000; from 600 to 13,000; from 700 to 12,000; from 800 to 11,000; from 900 to 10,000; from 1,000 to 9,000; from 1,100 to 8,000; from 1,200 to 7,000; from 1,300 to about 6,000; from 1,400 to 5,000; from 1, to 4,000; from 1,600 to 3,000; from 1,700 to 2,000; or from 1,800 to 1,900. In additional embodiments, c is an integer from 10 to about 19,000; from 100 to 18,000, from 200 to 17,000; from 300 to 16,000; from 400 to 15,000; from 500 to 14,000; from 600 to 13,000; from 700 to 12,000; from 800 to 11,000; from 900 to 10,000; from 1,000 to 9,000; from 1,100 to 8,000; from 1,200 to 7,000; from 1,300 to about 6,000; from 1,400 to 5,000; from 1,500 to 4,000; from 1,600 to 3,000; from 1,700 to 2,000; or from 1,800 to 1.900. With control over the variation in a, b and c, the practitioner is able to tune the physical properties of the biodegradable polymers.

Physical properties of the polymers in the present invention can be fine tuned so that the polymers can optimally perform for their intended use. Properties that can be fine tuned, without limitation, include Tg, molecular weight (both $M_n$ and $M_w$), polydispersity index (PDI, the quotient of $M_w/M_n$), degree of elasticity and degree of amphiphlicity. In one embodiment of the present invention, the Tg of the polymers range from about −25° C. to about 85° C. In still another embodiment of the present invention, the PDI of the polymers range from about 1.35 to about 4. In another embodiment of the present invention, the Tg of the polymers ranges form about 0° C. to about 40° C. In still another embodiment of the present invention, the PDI of the polymers range from about 1.5 to about 2.5.

The biodegradable polymers of the present invention, therefore, can be used to form and to coat implantable medical devices. The biodegradable polymers of the present invention are also useful for the delivery and controlled release of drugs. Drugs that are suitable for release from the polymers of the present invention include, but are not limited to, anti-proliferative compounds, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant micro-organisms, liposomes, and the like.

In one embodiment of the present invention, the drugs controllably released from the biodegradable polymer include, but are not limited to, macrolide antibiotics including FKBP-12 binding agents. Exemplary drugs of this class include sirolimus (rapamycin), tacrolimus (FK506), everolimus (certican or RAD-001), temsirolimus (CCI-779 or amorphous rapamycin 42-ester with 3-hydroxy-2-(hydroxymethyl)-2-methylpropionic acid as disclosed in U.S. patent application Ser. No. 10/930,487) and zotarolimus (ABT-578; see U.S. Pat. Nos. 6,015,815 and 6,329,386). Additionally, other rapamycin hydroxyesters as disclosed in U.S. Pat. No. 5,362,718 may be used in combination with the terpolymers of the present invention. The entire contents of all of preceding patents and patent applications are herein incorporated by reference for all they teach related to FKBP-12 binding compounds and their derivatives.

In one embodiment of the present invention, the drug is covalently bonded to the biodegradable polymer. The covalently-bound drug is released in situ from the biodegrading polymer with the polymer degradation products thereby ensuring a controlled drug supply throughout the degradation course. The drug is released to the treatment site as the polymeric material is exposed through biodegradation.

Coating implantable medical devices with biodegradable polymers that also control drug release is therapeutically advantageous to the patient. Post surgical complications involving medical device implants, e.g. vascular stents, are frequent. Administering drugs combating thrombosis, for example, is a common practice after surgical procedures, especially after cardiothoracic interventions. Drug releasing polymeric coatings on implanted medical devices can offset post surgical side effects by delivering therapeutic agents, such as drugs, directly to the affected areas.

Implantable medical devices suitable for use with the biodegradable polymers of the present invention include, but are not limited to, vascular stents, stent grafts, urethral stents, bile duct stents, catheters, guide wires, pacemaker leads, bone screws, sutures and prosthetic heart valves.

The biodegradable polymers of the present invention can be applied to medical device surfaces, either primed or bare, in any manner known to those skilled in the art. Applications methods compatible with the present invention include, but are not limited to, spray coating, electrostatic spray coating, plasma coating, dip coating, spin coating and electrochemical coating.

The biodegradable polymers can be coated on all surfaces of an implantable medical device or only a portion of the medical device such that the medical device contains portions that provide the beneficial effects of the coating and portions that are uncoated. The coating steps can be repeated or the methods combined to provide a plurality of layers of the same coating or a different coating. In one embodiment, each layer of coating comprises a different polymer or the same polymer. In another embodiment each layer comprises the same drug or a different drug.

Furthermore, the biodegradable polymer-containing medical device can further comprise a top, or cap, coat. A cap coat as used here refers to the outermost coating layer applied over another coating. A drug-releasing polymer coating is optionally applied over the primer coat. A polymer cap coat is applied over the biodegradable polymer coating. The cap coat may optionally serve as a diffusion barrier to further control the drug release, or provide a separate drug. The cap coat may be merely a biocompatible polymer applied to the surface of the sent to protect the stent and have no effect on elution rates. An exemplary cap coat is a copolymer of lactide.

Depending upon the type of materials used to form the coatings of the present invention, the coatings can be applied to the surface of a medical device through any of the coating processes known or developed in the art. One method includes directly bonding the coating to the implant's surface. By directly attaching the polymer coating to the implant, covalent chemical bonding techniques are utilized. Generally, the implant surface possesses chemical functional groups on its surface such as carbonyl groups, primary amines, hydroxyl groups, or silane groups which will form strong, chemical bonds with similar groups on the active compounds utilized. In the absence of such chemical forming functional group, known techniques can be utilized to activate the material's surface before coupling the biological compound. Surface activation is a process of generating, or producing, reactive chemical functional groups using chemical or physical techniques such as, but not limited to, ionization, heating, photochemical activation, oxidizing acids, and etching with strong organic solvents.

Alternatively, the coating can be indirectly bound to the implant's surface through an intermediate layer. This intermediate layer can be either covalently bound to the fixed substrate's surface or bonded through intermolecular attractions such as ionic or Van der Waals forces. Examples of commonly used intermediate layers within the scope of the present invention include, but are not limited to, organic polymers such as silicones, polyamines, polystyrene, polyurethane, acrylates, methoxysilanes, and others.

According to the teachings of the present invention, the implant also can be provided with a non-erodible base coating. The base coating can be provided so as to enhance the biocompatibility of the implant. Exemplary base coatings can be selected from the group consisting of polyurethanes, silicones and polysilanes. Other polymers that can be utilized include polyolefins, polyisobutylene and ethylene-alphaolefin copolymers; acrylic polymers and copolymers, ethylene-co-vinylacetate, polybutylmethacrylate; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; polycarbonates; polyoxymethylenes; polyimides; polyethers; epoxy resins; polyurethanes; rayon; rayon-triacetate; cellulose; cellulose acetate, cellulose butyrate; cellulose acetate butyrate; cellophane; cellulose nitrate; cellulose propionate; cellulose ethers; and carboxymethyl cellulose. In accordance with the teachings of the present invention, the base coating can also include, without limitation, antibiotics, anti-inflammatory agents, lubricity-enhancing agents, anti-coagulants, anti-metabolites, anti-thrombogenic agents, immunosuppressive agents, muscle relaxants, proteins, peptides, and hormones.

In one embodiment of the present invention, an polymer of the present invention is chosen for a particular use based upon its physical properties. In one non-limiting example, a polymer coating provides additional structural support to a medical device by increasing the content of lactic acid in the polymer. In still another embodiment, a polymer coating on a medical device decreases friction between the medical device and the surrounding tissue, or between the medical device and the delivery system, facilitating the implantation procedure.

The biodegradable polymers described herein can be tuned to biodegrade at various lengths of time by varying the monomer composition of the polymer. In non-limiting examples, a polymer synthesized with polyethylene glycol monomers will be more hydrophilic than polymers without PEG monomers and therefore will have faster degradation times.

EXAMPLES

The following non limiting examples provide methods for the synthesis of exemplary polymers according to the teachings of the present invention.

Example 1

Synthesis of a Polymer of Formula 6

γ-Butyrolactone and ε-caprolactone were purified by vacuum distillation over calcium hydride. A dried serum bottle was charged with 24.00 g of γ-butyrolactone, 5.40 g of L-lactide and 0.60 g of ε-caprolactone, 0.0181 g of 1,8-otanediol and 15.4 mg of Tin (II) octoate in a glovebox. The bottle was sealed and heated in an oil bath at 140° C. for 5 days. The polymer was purified by first precipitation in water, second precipitation in methanol from 2-butanone solution.

The polymer was dried in vacuum at 50° C. overnight. An elastomeric material (D216-1626_042 in Table 1) was obtained.

Example 2

Synthesis of a Polymer of Formula 7

γ-Butyrolactone was purified by vacuum distillation over calcium hydride. Trimethylene carbonate, L-lactide and Al(i-PrO)$_3$ were used as received. A glass serum bottle was charged with 0.0185 g of Al(iPrO)$_3$, 3.00 g of γ-butyrolactone, 3.00 g of trimethylene carbonate and 4.00 g of lactide in a dry box. The bottle was then sealed, taken out of the dry box and put into an oil bath set at 130° C. for 1 hr with stirring and then the oil bath was cooled to 120.9° C. The polymerization was continued for 7 hr and stopped by taking the bottle out of the oil bath and cooling to room temperature. Chloroform was added into the bottle to dissolve the resultant polymer. Two to three drops of HCl were added to further terminate the polymerization. The dissolved polymer was then precipitated in MeOH (containing a few drops of HCl) and collected. The dissolving-precipitation steps were repeated twice or more and the resulting polymer, D281-1646-35 (Table 1), was dried in vacuum oven.

Example 3

Synthesis of a Polymer of Formula 8

A glass serum bottle was charged with 0.0185 g of Al(iPrO)$_3$, 3.50 g of γ-butyrolactone, 3.50 g of trimethylene carbonate and 3.00 g of glycolide in a dry box. The bottle was then sealed, taken out of the dry box and put into an oil bath set at 130° C. for 1 hr with stirring and then the oil bath was cooled down to 120.9° C. The polymerization continued for 7 hr and was stopped by taking the bottle out of the oil bath and cooling to room temperature. The reactants turned to a white solid within two hours. The resulting polymer is D301-1646-46 (Table 1).

Example 4

Synthesis of a Polymer of Formula 9

A glass serum bottle was charged with 0.037 g of Al(iPrO)$_3$, 6.00 g of γ-butyrolactone, 6.00 g of trimethylene carbonate, 8.00 g of lactide and 2.00 g of glycolide in a dry box. The bottle was the sealed, taken out of the dry box and put into an oil bath set at 130° C. and the polymerization was carried out for 15 hr before being stopped by taking the bottle out of the oil bath and cooling to room temperature. Chloroform was added into the bottle to dissolve the polymer. Two to three drops of HCl were added to further terminate the polymerization. The dissolved polymer was precipitated in MeOH (containing a few drops of HCl) and collected. The dissolving-precipitation step was repeated twice more and the resulting polymer, D305-1646-47 (Table 1), was dried in vacuum oven.

Example 5

Synthesis of a Polymer of Formula 10

A glass serum bottle was charged with 0.85 g PEG3400, 0.0180 g Al(iPrO)$_3$ 3.00 g γ-butyrolactone, 3.00 g trimethylene carbonate and 4.00 g lactide in a dry box. The bottle was then sealed, taken out of the dry box and put into an oil bath set at 100° C. and stirred for 96 hr. The reaction was stopped by taking the bottle out of the oil bath and cooling to room temperature. Chloroform was added into the bottle to dissolve the polymer. Two to three drops of HCl were added to further terminate the polymerization. The dissolved polymer was precipitated in MeOH (containing a few drops of HCl) and collected. The dissolving-precipitation step was repeated twice more and the resulting polymer, D284-1646-42-PEG3400 (Table 1), was dried in vacuum oven.

Example 6

Characterization of Biodegradable Polymers

Table 1 contains characterization data on exemplary controlled release biodegradable polymers of the present invention synthesized by the methods of Examples 1-5. In the table the monomers are coded as following.
γBL=γ-butyrolactone
DLLA=D,L-lactide
LLA=L-Lactide
TMC=trimethylene carbonate
CL=ε-caprolactone
PEG=poly(ethylene glycol)

Compositions of polymers were determined by proton NMR from integrals of individual monomers. Relative molecular weight and its distribution were determined by gel permeation chromatograph in THF and the columns were calibrated with narrow polystyrene standards. Glass transition temperature was determined with differential scanning calorimetry at a heating rate of 20° C./min.

TABLE 1

| Polymer (synthesis conditions) | Monomer | feeding ratio wt % | final ratio molar % | Mn (g/mol) | Mw (g/mol) | PDI | Tg (° C.) |
|---|---|---|---|---|---|---|---|
| D215-1626-038-#4 | rBL/LLA | 80/20 | 15/85 | 21150 | 29301 | 1.39 | 37.99 |
| D216-1626_042 | rBL/CL/LLA | 80/2/18 | 14.2/5.3/80.5 | 36003 | 55085 | 1.53 | 20.77 |
| D260-1646-29 | γBL/TMC/LLA | 50/20/30 | 11.4/21.5/67.1 | 22751 | 37967 | 1.67 | 31.94 |
| D261-1646-29 | γBL/TMC/LLA | 50/15/35 | 9.0/13.4/77.6 | 26979 | 48021 | 1.78 | 39.63 |
| D262-1646-29 | γBL/TMC/LLA | 50/10/40 | 6.0/9.1/84.9 | 23232 | 47423 | 2.04 | 38.81 |
| D271-1678-50 | γBL/TMC/LLA | 20/16/64 | 7.49/26.29/66.22 | 40422 | 72581 | 1.80 | 24.93 |
| D272-1678-50 | γBL/TMC/LLA | 10/18/72 | 3.98/24.56/71.47 | 41072 | 77908 | 1.90 | 29.71 |
| D273-1646-32 | γBL/TMC/DLA | 50/15/35 | 5.4/13.0/81.6 | 25493 | 38773 | 1.521 | 37.34 |
| D274-1646-32 | γBL/TMC/DLA | 50/10/40 | 10.1/6.0/83.9 | 26736 | 54236 | 2.029 | 39.61 |
| D275-1646-32 | γBL/TMC/LLA | 40/30/30 | 9.4/14.7/75.9 | 31833 | 47171 | 1.482 | 44.19 |
| D276-1646-32 | γBL/TMC/LLA | 30/40/30 | 10.8/56.4/32.8 | 41220 | 77148 | 1.872 | 6.4 |
| D277-1646-33 | γBL/TMC/LLA | 30/40/30 | 12.0/57.4/30.6 | 6350 | 19021 | 3.00 | −0.14 |
| D278-1646-33 | γBL/TMC/LLA | 40/30/30 | 14.4/51.1/34.5 | 8476 | 17943 | 2.12 | 2.81 |

TABLE 1-continued

| Polymer (synthesis conditions) | Monomer | feeding ratio wt % | final ratio molar % | Mn (g/mol) | Mw (g/mol) | PDI | Tg (°C.) |
|---|---|---|---|---|---|---|---|
| D279-1678-51 | γBL/TMC/LLA | 80/2/18 | 19.85/25.54/55.52 | 14384 | 21371 | 1.49 | 14.65 |
| D280-1646-34 | γBL/TMC/LLA | 53.3/26.7/20 | 21.4/51.0/27.6 | 24584 | 48682 | 1.98 | −1.25 |
| D281-1646-35 | γBL/TMC/LLA | 30/30/40 | 10.3/40.5/49.2 | 30239 | 61052 | 2.02 | 18.05 |
| D282-1646-35 | γBL/TMC/LLA | 30/20/50 | 9.7/21.7/68.6 | 37286 | 69784 | 1.89 | 33.19 |
| D283-1646-37 | γBL/TMC/DLLA | 30/25/45 | 8.0/30.1/61.9 | 29189 | 52256 | 1.79 | 24.07 |
| D284-1646-37 | γBL/TMC/DLLA | 30/30/40 | 13.1/44.1/42.9 | 21980 | 35853 | 1.63 | 7.53 |
| D284-1646-42-PEG3400 | PEG3400/γBL/TMC/DLLA | 0.85/30/30/40 | 0.05/5.59/32.18/62.17 | 17640 | 26038 | 1.48 | 2.25 |
| D285-1646-37 | γBL/TMC/DLLA | 30/35/35 | 12.7/51.5/35.9 | 19777 | 36324 | 1.84 | 1.27 |
| D286-1646-37 | γBL/TMC/DLLA | 30/40/30 | 11.8/59.5/28.7 | 17157 | 31649 | 1.85 | −2.56 |
| D291-1646-43 | γBL/TMC/DLLA | 30/30/40 | 11.4/33.4/55.2 | 33917 | 61792 | 1.82 | 17.34 |
| D291-1646-45 | γBL/TMC/DLLA | 30/30/40 | 10.2/37.3/52.5 | 45165 | 81081 | 1.80 | 15.70 |
| D292-1646-43 | γBL/TMC/DLLA | 30/30/40 | 7.0/25.0/68.0 | 18391 | 41109 | 2.24 | 24.90 |
| D293-1646-44 | γBL/TMC/DLLA | 30/30/40 | 7.6/14.6/77.8 | 21809 | 40302 | 1.85 | 32.03 |
| D294-1646-44 | γBL/TMC/DLLA | 30/30/40 | 12.8/20.8/66.4 | 32639 | 61661 | 1.89 | 30.37 |
| D299-1646-45 | γBL/TMC/DLA | 30/25/45 | 11.8/29.1/59.1 | 42245 | 79327 | 1.88 | 20.86 |
| D300-1646-46 | γBL/TMC/LLA | 30/25/45 | 10.2/20.1/69.6 | 39002 | 69722 | 1.79 | 39.29 |
| D305-1646-47 | γBL/TMC/DLA/GA | 3/3/4/1 | 8.4/38.7/41.3/11.6 | 44555 | 83317 | 1.87 | 15.88 |
| D306-1646-47 | γBL/TMC/GA | 30/55/15 | 10.5/67.2/22.3 | 41423 | 60084 | 1.45 | −14.42 |
| D307-1646-48 | γBL/TMC/DLA | 30/22.5/47.5 | 9.4/22.7/67.9 | 40760 | 74219 | 1.83 | 27.43 |
| D308-1646-48 | γBL/TMC/DLA | 30/20/50 | 7.1/21.1/71.8 | 42525 | 73792 | 1.82 | 29.62 |

Example 7

Fabricating Implantable Vascular Stents

The present invention pertains to biodegradable polymers used for the manufacture of medical devices and medical devices coatings. The biodegradable polymers disclosed in the present invention retain and release bioactive drugs. Example 6 discloses a non-limiting method for fabricating stents made of biodegradable polymers according to the teachings of the present invention.

For exemplary, non-limiting, purposes a vascular stent will be described. A biodegradable polymer is heated until molten in the barrel of an injection molding machine and forced into a stent mold under pressure. After the molded polymer (which now resembles and is a stent) is cooled and solidified the stent is removed from the mold. In one embodiment of the present invention the stent is a tubular shaped member having first and second ends and a walled surface disposed between the first and second ends. The walls are composed of extruded polymer monofilaments woven into a braid-like embodiment. In the second embodiment, the stent is injection molded or extruded. Fenestrations are molded, laser cut, die cut, or machined in the wall of the tube. In the braided stent embodiment monofilaments are fabricated from polymer materials that have been pelletized then dried. The dried polymer pellets are then extruded forming a coarse monofilament which is quenched. The extruded, quenched, crude monofilament is then drawn into a final monofilament with an average diameter from approximately 0.01 mm to 0.6 mm, preferably between approximately 0.05 mm and 0.15 mm. Approximately 10 to approximately 50 of the final monofilaments are then woven in a plaited fashion with a braid angle about 90 to 170 degrees on a braid mandrel sized appropriately for the application. The plaited stent is then removed from the braid mandrel and disposed onto an annealing mandrel having an outer diameter of equal to or less than the braid mandrel diameter and annealed at a temperature between about the polymer glass transition temperature and the melting temperature of the polymer blend for a time period between about five minutes and about 18 hours in air, an inert atmosphere or under vacuum. The stent is then allowed to cool and is then cut.

Example 7

Coating Implantable Vascular Stents

A 1% solution of a biodegradable polymer (such as from Examples 1-5) and ABT-578 (a polymer:drug ratio of 70:30 by weight) in chloroform was sprayed on a vascular stent and allowed to dry producing a controlled release coating on the vascular stent. The release of drug from the stent into an elution media was measured by high performance liquid chromatography (HPLC).

Figure 2:
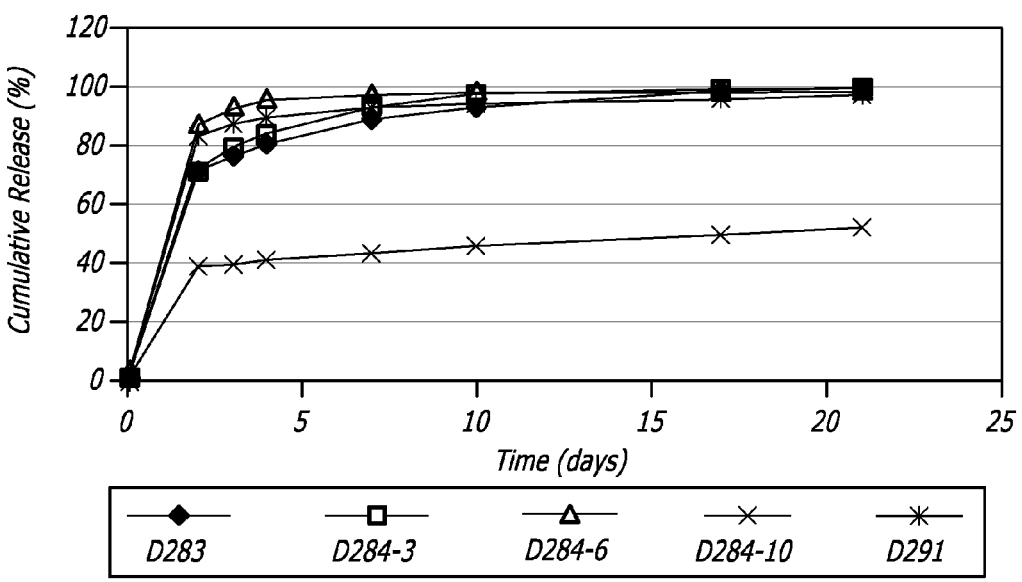
FIG. 2 depicts the release of rapamycin from biodegradable polymer-coated stents according to the teachings of the present invention.
Figure 3:
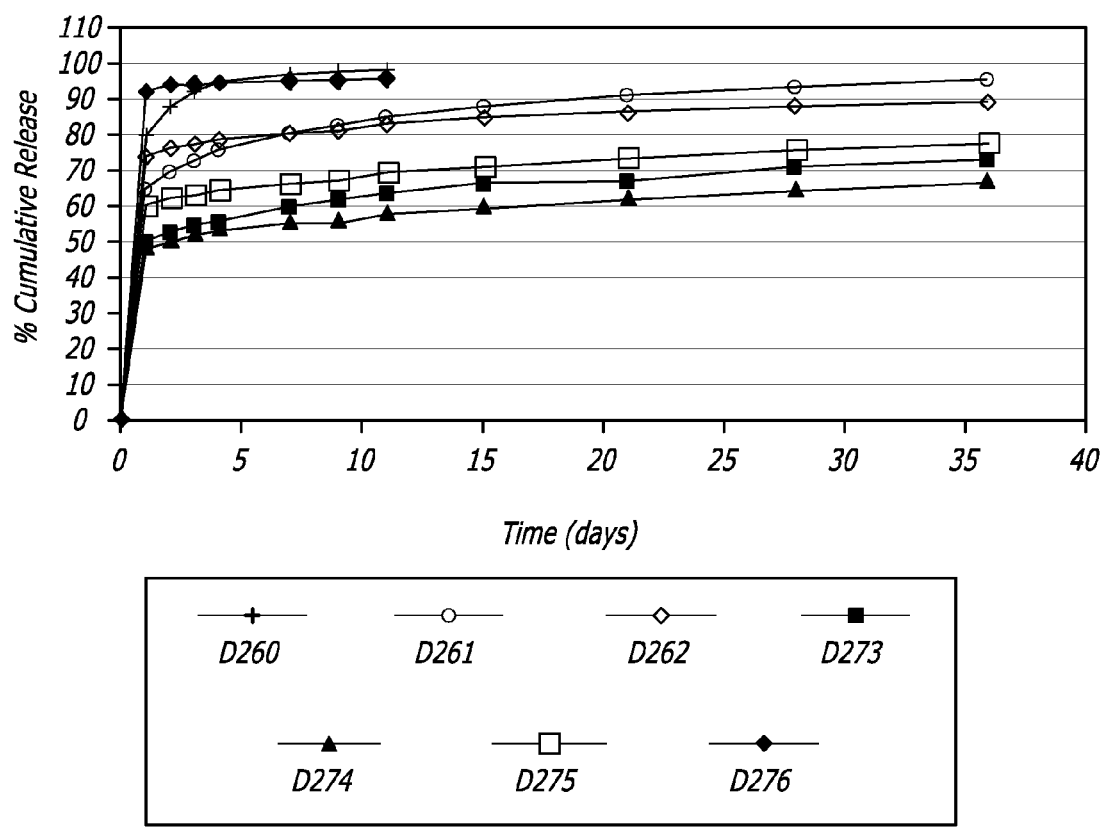
FIG. 3 depicts the release of rapamycin from biodegradable polymer-coated stents according to the teachings of the present invention.

The drug elution profiles of ABT-578 and rapamycin from polymers and stents coated with the exemplary polymer of the present invention are depicted in FIG. 1 (ABT-578 release from various polymers at various drug loading percentages), FIG. 2 (rapamycin release from various polymers) and FIG. 3 (rapamycin release from polymer-coated stents).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An implantable medical device having a controlled release biodegradable polymer coating thereon, wherein the polymeric coating comprises:
    a polymer of the general structure of Formula 6:

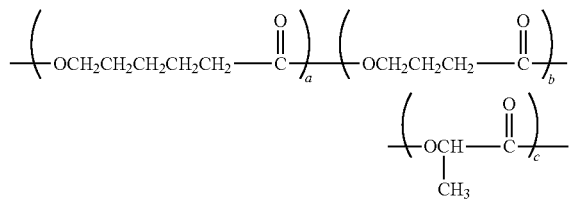

Formula 6 wherein a is an integer from 1 to about 20,000;
b is an integer from about 1 to about 20,000;
c is an integer from about 1 to about 20,000; and
the sum of a, b and c is at least 3; and
at least one drug selected from the group consisting of FKBP-12 binding agents, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides and transforming nucleic acids.

2. The implantable medical devices of claim 1 wherein said drug comprises at least one compound selected from the group consisting of sirolimus, tacrolimus, everolimus, temsirolimus and zotarolimus.

3. The implantable medical device of claim 2 wherein said drug comprises zotarolimus.

4. The implantable medical device of claim 1 wherein said medical device is selected from the group consisting of vascular stents, stent grafts, urethral stents, bile duct stents, catheters, guide wires, pacemaker leads, bone screws, sutures and prosthetic heart valves.

5. The implantable medical device of claim 4 wherein said medical device is a vascular stent.

6. The implantable medical device of claim 1 wherein said medical device further comprises a cap coat.

* * * * *